(12) United States Patent
Berard et al.

(10) Patent No.: US 9,474,823 B2
(45) Date of Patent: Oct. 25, 2016

(54) LOW DISPERSION SCENT SAMPLER FOR POINT OF SALE DISPLAY

(71) Applicants: James Berard, Pleasantville, NY (US); Tom Lockwood, Winston-Salem, NC (US)

(72) Inventors: James Berard, Pleasantville, NY (US); Tom Lockwood, Winston-Salem, NC (US)

(73) Assignees: Scentisphere LLC, Carmel, NY (US); Rock-Tenn Shared Services, LLC, Norcross, GA (US)

( * ) Notice: Subject to any disclaimer, the term of this patent is extended or adjusted under 35 U.S.C. 154(b) by 161 days.

(21) Appl. No.: 14/540,550

(22) Filed: Nov. 13, 2014

(65) Prior Publication Data

US 2015/0130087 A1    May 14, 2015

Related U.S. Application Data

(60) Provisional application No. 61/903,678, filed on Nov. 13, 2013.

(51) Int. Cl.
*B01F 3/04* (2006.01)
*A61L 9/12* (2006.01)
*A61L 9/04* (2006.01)

(52) U.S. Cl.
CPC ............ *A61L 9/122* (2013.01); *A61L 9/048* (2013.01); *B01F 3/04085* (2013.01)

(58) Field of Classification Search
CPC .. B01F 3/04; B01F 3/04085; B01F 3/04007; A45D 34/02
USPC ............................. 261/26, 30, 104, DIG. 88
See application file for complete search history.

(56) References Cited

U.S. PATENT DOCUMENTS 5,898,475 A * 4/1999 Martin ................ A61L 9/127
352/40

* cited by examiner

*Primary Examiner* — Robert A Hopkins
(74) *Attorney, Agent, or Firm* — Levine Mandelbaum PLLC

(57) ABSTRACT

A low dispersion scent sampler for point of sale display has a housing with a front panel to which a label advertising products sold at the point of sale may be affixed. Inside of the housing is a blower connected to a timer control circuit and battery through a pushbutton actuated switch. A scented material is provided in the air flow path from the blower to one or more exhaust ports. When the pushbutton is pressed by a consumer, the blower turns on for a brief period of time to force air over the scented material and then through the exhaust ports for sampling of the scent emitted by the scented material. The on time for the blower is brief to limit exposure to the scent to the space occupied by the consumer.

10 Claims, 16 Drawing Sheets

LOW DISPERSION SCENT SAMPLER FOR POINT OF SALE DISPLAY

BACKGROUND OF THE INVENTION

Enabling scent sampling at a point of sale is a highly effective tool for increasing sales of perfumes, colognes, and other scented products.

Fragrance perfume companies display tester bottles with actual fragrance at counters in cosmetic and department stores. This is very costly due to pilferage and breakage. Sales consultants are also sometimes employed to introduce customers to a fragrance product. This is highly costly and may causes ill-will when the consultants are perceived by shoppers to pressure them or otherwise intrude on their privacy.

The growth of self service stores which sell fragrance products has increased the incidence of problems associated with the display tester bottles which, when left for customers to try, are often stolen. Neither retail stores nor consumer product good companies want consumers to open products or spray their products at the point of sale as is commonly done in the absence of another opportunity for scent sampling. Opening of products at the point of sale makes the product vulnerable to tampering and spillage, creates shortages, and can make the retailers and consumer product good companies liable for any resulting harm. Locking the product in display cases which must be opened by sales personnel upon request defeats the spontaneity which results in impulse purchases.

There are many scent emitting appliances capable of dispersing large volumes of fragrance molecules through a space such as that of a hotel lobby or room, an entire store, or a bathroom.

U.S. Pat. No. 6,631,888 to Prueter for a Battery Operated Fragrance Dispenser discloses a scent sampler in which a fan is actuated in response to having a shell engage a cap.

U.S. Pat. No. 5,069,876 to Oshinsky for a Combined Scent and Audio Point of Sale Display Unit discloses a point of sale display having a tape player for delivering an audio message and a device for delivering a scent.

U.S. Patent Publication No. 2005/0226788 by Hrybyk et al. for an Air Scenting Apparatus discloses a basic device having inlet and outlet ports with a scented material in the path between the ports and a fan arranged to draw air into the device through the inlet port after which the air is scented and then expelled from the device through the outlet port.

U.S. Pat. No. 4,603,030 to McCarthy for Scent-Emitting Systems discloses a device which can deliver a series of different scents, one after the other.

U.S. Pat. No. 7,363,737 to Benalikhoudja for an Advertising Display with the Diffusion of Scents discloses a rectangular sign for displaying an advertising message. Between the front and rear panels of this sign is a chamber in which compressed air and a scented fluid are mixed. The scented air is then expelled through a port for delivery of the scent to the viewer of the sign.

U.S. Pat. No. 7,691,336 to Westring for Devices and Systems for Dispensing Volatile Materials discloses an apparatus having a rotating tray with compartments that hold various scented materials. A heater is provided which sequentially heats each of the scented materials as the tray brings them into alignment with the heater. A fan is provided to diffuse the scent emitted from the heated material.

U.S. Pat. No. 7,040,548 to Rodgers for a Residual Free Scent Dispenser and Method discloses a hunting device used for attracting game by emitting a scent. The device has an inlet port, an outlet port, a fan for drawing air from the inlet port through the outlet port and a scented material in the path to the outlet port.

U.S. Patent Publications Nos. 2002/0158351 and 2002/0048530 by Wohrle for a Scent Delivery System disclose a device having several cartridges containing scented fluids seated within pockets in a tray. The materials are heated to form scented vapors which are delivered to the outside of the device by a fan.

U.S. Patent Publication No. 2006/0175426 by Schramm et al. for Dispensing of Multiple Volatile Substances discloses a device for emitting multiple scents into a large area such as a room or larger region.

U.S. Pat. No. 6,136,277 to Nardini for a Fragrance Dispersion System discloses a device which can produce multiple scents in synchronization with an audio or video program. The device has multiple scent ports containing scented materials. Each of the ports is opened and closed by a gate. The audio-visual program controls the opening and closing of the gates to release the desired scents at the appropriate time in synchronization with the program. A fan is present for expelling the scented air to the exterior of the device.

U.S. Pat. No. 5,887,118 to Huffman et al. for an Olfactory Card discloses a device in which a scent is delivered by heating a scented material in response to application of electricity. The application of electricity is controlled by a computer which may have a touch screen.

The foregoing machines are designed to disperse a strong scent into a large area. These devices are not targeted scent sampling machines, but are scent diffusion machines designed to fill a voluminous area with large quantities of fragrance particles or molecules.

Because scent diffusers of the prior art are designed to flood a large area with scent they are unsuitable for use in a small defined space within a retail shopping environment, i.e., where competitive products are being merchandised, as the scent of one brand's product cannot be permitted to penetrate the selling space assigned to a competitor's product. Such scent dispersion machines are, therefore, generally unwelcome in stores offering competitive scented products for sale.

In addition, prior art scent dispersing machines are often cumbersome and too large for placement in the confined shelf and counter areas of retail stores. Their use can also be costly to fragrance product suppliers who must pay, as is often the case, for a share of limited shelf and counter space to sell their products. Filling such space with the relatively large scent dispersion machines of the prior art can result in a need for increased space for the product to be sold assuming that such space is even available.

All the appliances sited in the above patents are self contained products designed to perform the unilateral function of dispersing strong scent to a large group of recipients in a large area. None of these designs are miniature in design or simple enough to be economically incorporated into existing point of purchase displays or collateral in-store advertising programs of the manufacturers of scented products. None of the prior art scent dispersion devices is designed to easily transform conventional point of sale displays to permit scent sampling.

SUMMARY OF THE INVENTION

The present invention overcomes the aforementioned problems of the prior art by dispersing a low level of fragrance molecules in response to a demand action executed by a shopper. The invention satisfies the shopper's curiosity and desire to sample the scent without violating the personal space of shoppers who may not be interested in experiencing the scent.

The invention includes a scent sampler for use in a point-of-purchase display for perfume or the like, in which a small fan blows air over a gel containing a scented oil or scented beads or pellets. The scented air exits an exhaust port in the housing. The fan is operated by a pushbutton switch in series with a battery. The exhaust port and pushbutton switch may be mounted remotely from the housing by placing flexible plastic tubing between an opening in the chamber housing the scented gel and extending wires between the pushbutton switch, fan, and battery. The housing can be mounted within a point of purchase display so that only the exhaust port and pushbutton are visible and accessible on the outside.

Additional features include the possibility of having multiple gels with different scents in separate chambers in the housing. Passageways between the chambers and fan could be opened and closed to select one of the scents to be sampled.

Instead of a simple pushbutton, a touch screen displaying an ad for the perfume could be touched to actuate the fan and open the passageway to a chamber having the desired scent or the scent could be released under control of a computer program with or without audio-visual accompaniment.

It is an object of the invention to provide a miniature scent dispersing mechanism which can be activated "on demand" by a customer.

Another object of the invention is to provide a miniature scent dispersing mechanism that can be easily and inexpensively fitted into existing point of sale store display Still another object of the invention is to provide a machine which, when activated by a consumer, will disperse a volume of air with a low dosage of fragrance particles, for a short predetermined amount of time, that only the consumer will experience.

A further object of the invention is to provide a scent sampler which discontinues dispensing a scent within seconds of being released.

Still a further object of the invention is to provide a sampler with a timing circuit for limiting the period of emission of scent into a small space so that the scent is not readily detected in adjacent spaces.

Other and further objects of the invention will be apparent from the following description and the annexed drawings of a preferred embodiment of the invention.

DESCRIPTION OF THE PREFERRED EMBODIMENT

Figure 1:
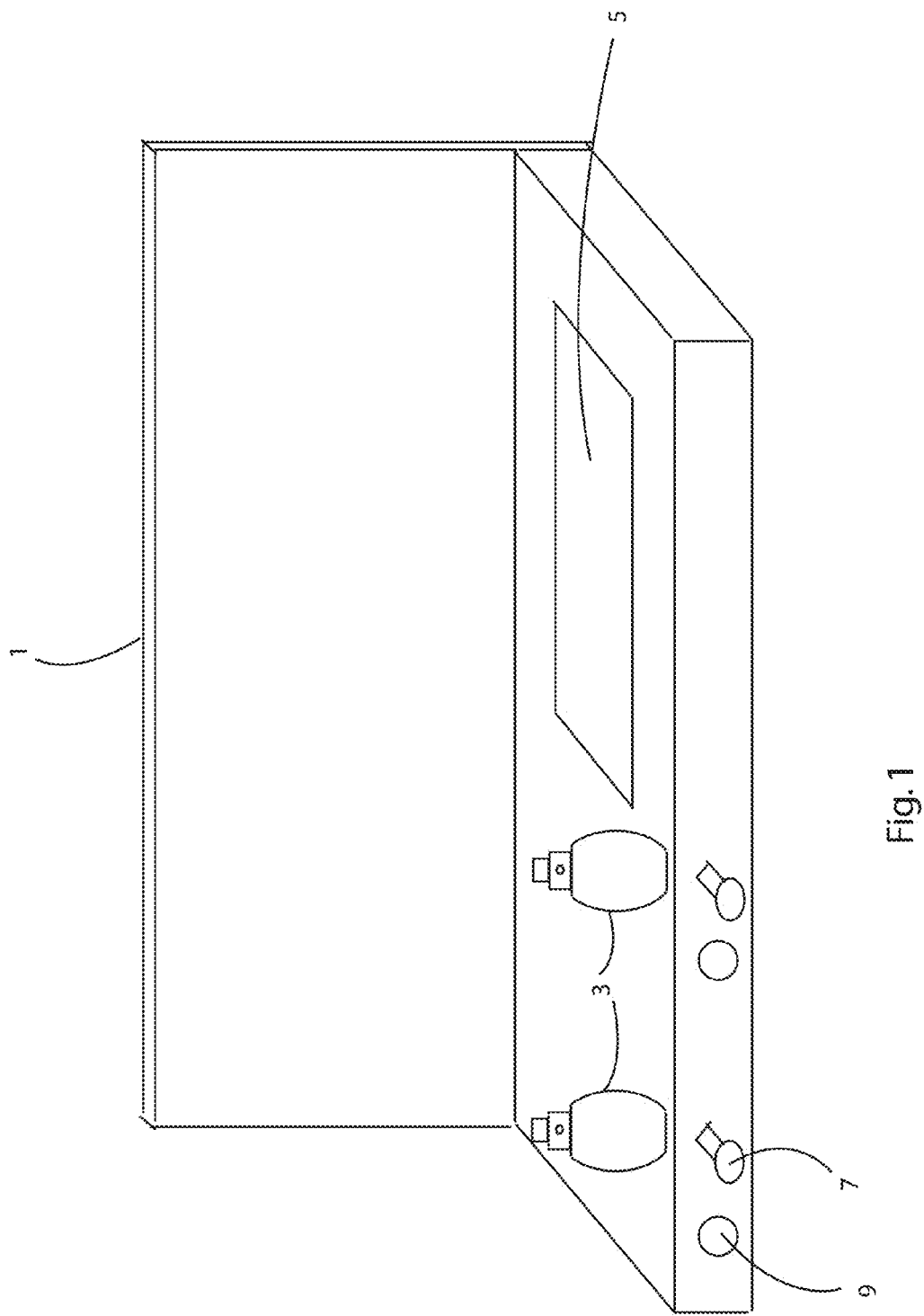
FIG. 1 is a perspective view of the apparatus of a first preferred embodiment of the invention.

Referring now to FIG. 1 of the drawings there is shown a first preferred embodiment of a display unit 1 having a vertical rectangular front facing panel 6 on which an advertiser's graphics and/or text message can be displayed. The content of the displayed graphics and message may be composed to promote the scented products being offered for sale at a point of purchase in a cosmetics store or cosmetics department of a department store whereat the display 1 is situated.

Atop the display are perfume bottles 3, or replicas thereof which simulate the appearance of actual containers of perfume, cologne, toilet water or other scented products. Normally the bottles 3 will not be functional but only illustrative of the actual scented product. That is, they will not be functional to spray a sample of the scented product contained in bottles. The perfume bottles or containers 3 may be affixed to the display to prevent easy removal in order to avoid pilferage.

A rectangular cutout is optionally provided in the cardboard display to form a compartment in the display for storing ready-for-sale packaged perfume bottles filled with perfume of the type to be sampled at the display. The bottles of scented product offered for sale can be packaged in sealed cartons or similar containers which may be tamperproof and tagged to prevent pilferage as will be known to those skilled in the art.

In order for a customer to sample a perfume of the type sold in a bottle of which a display bottle 3 is a replica, there is provided on the front lower edge of the display 1 a pushbutton 7 which a shopper may press to close a switch 6 (FIG. 3) for expelling a limited burst of scented vapor into the space occupied by the shopper through a port 9.

Figure 2:
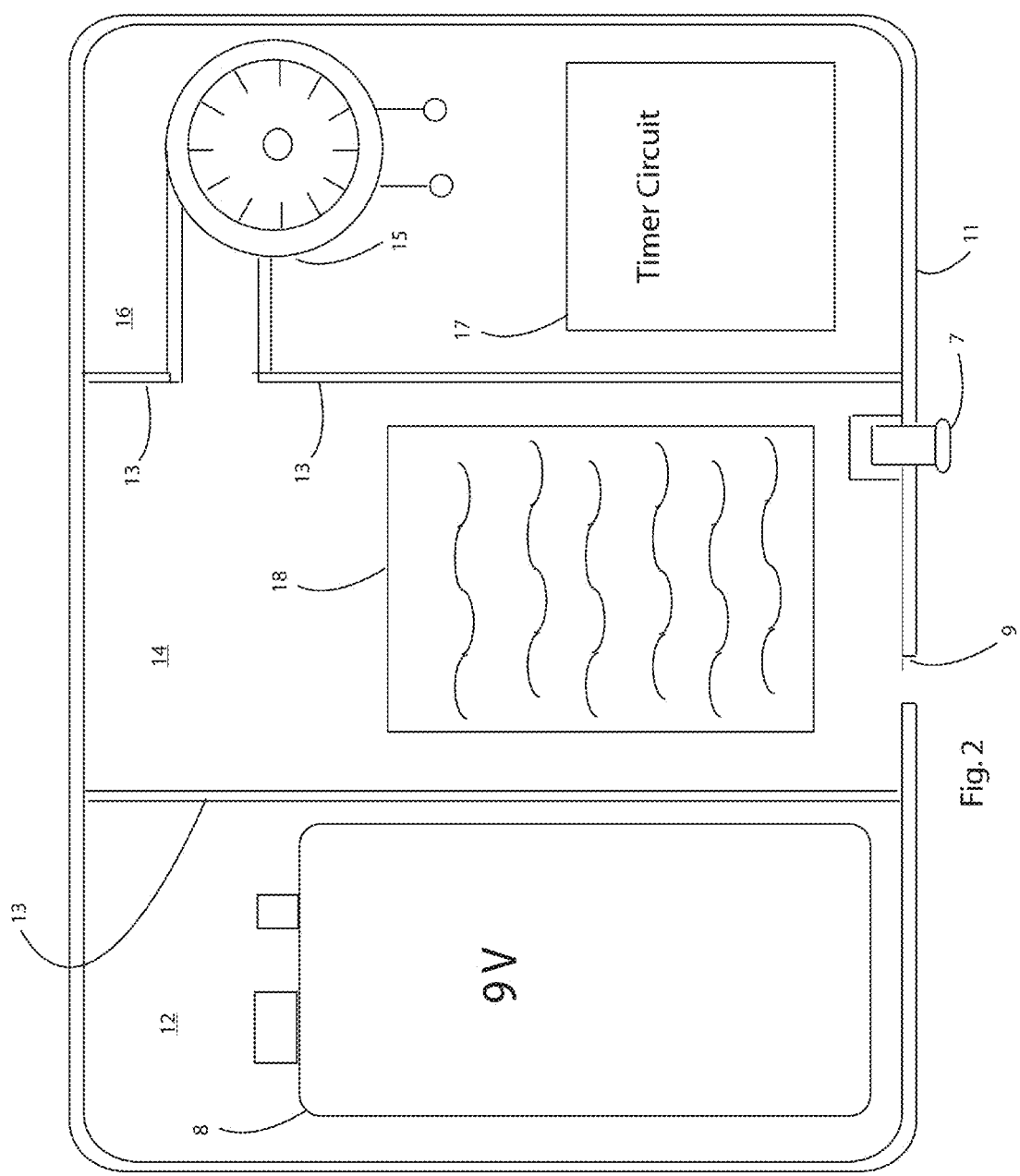
FIG. 2 is a top plan view of a component of the apparatus of the first preferred embodiment of the invention.

As can be best seen in FIG. 2 of the drawings, the pushbutton 7 for closing a switch 6 is mounted in the front panel of a rectangular housing of a scent sampling module 10 which is shown with its top rectangular planar cover removed. The housing 11 of the scent sampling module 10 is divided by walls 13 into 3 compartments. Inside of the leftmost compartment 12, as seen in FIG. 2, is a standard nine volt battery 8.

The central compartment 14 contains a sample of material having the scent to be sampled. In the preferred embodiment of the invention the scent is contained in a gel 18 having, as a component, a fragrance oil which emits the scent is to be sampled mixed with an alcohol.

In order to expel scented air from inside the module 10 to the ambient atmosphere through the port 9, there is provided a blower 15 in the form of a low DC voltage small, low inertia blade squirrel cage fan housed within the third compartment 16 of housing 11. The fan of the blower 15 is one which quickly instantly reaches maximum rotational speed when energized by the voltage of the battery 8. In the preferred embodiment of the invention the fan has a flat fan outer housing with dimensions of 15 mm×15 mm×4 mm, i.e., approximately the size of a nickel coin. Such a fan is distributed by MCM Distributors as part number 1504. The miniature size of the flat fan unit enables it to easily fit into a module small enough to be secreted within most common point of sale displays.

Other fans of similar size and propulsion characteristics may be used in accordance with the teachings of the invention. Such fans may require a power source other than a 9 volt battery in which case the battery 8 can be replaced with a suitable power supply, ac or dc, or a battery of different voltage as will be known to those skilled in the art.

When actuated, the fan 15 moves air from the third compartment 16 into the second compartment 14 thereby increasing the air pressure within the second compartment. The high pressure air in the second compartment, throughout which the scent from the gel 18 has dispersed, is forced through the port 9 to the lower pressure external ambient atmosphere. A vapor of the scent which is emitted by the scented oil contained within the second compartment exits the port 9 with the high pressure air where the scent can be sniffed and sampled by a consumer.

A timing circuit 17 is also housed in the third compartment to control the duty cycle of the fan when actuated by pressing the pushbutton 7. The electrical circuit for operating the fragrance sampler will now be described with respect to FIG. 3.

The small fan is positioned upstream of the gel fragrance pod 18 made up of fragrance oil and alcohol. The fan disperses as little as 1/10th or less of the amount of fragrance particles in a specified area versus prior art scent dispersion devices. The timer circuit limits the on time of the fan so that the fragrance dispersion is targeted to only the shopper who actuates the device.

Figure 3:
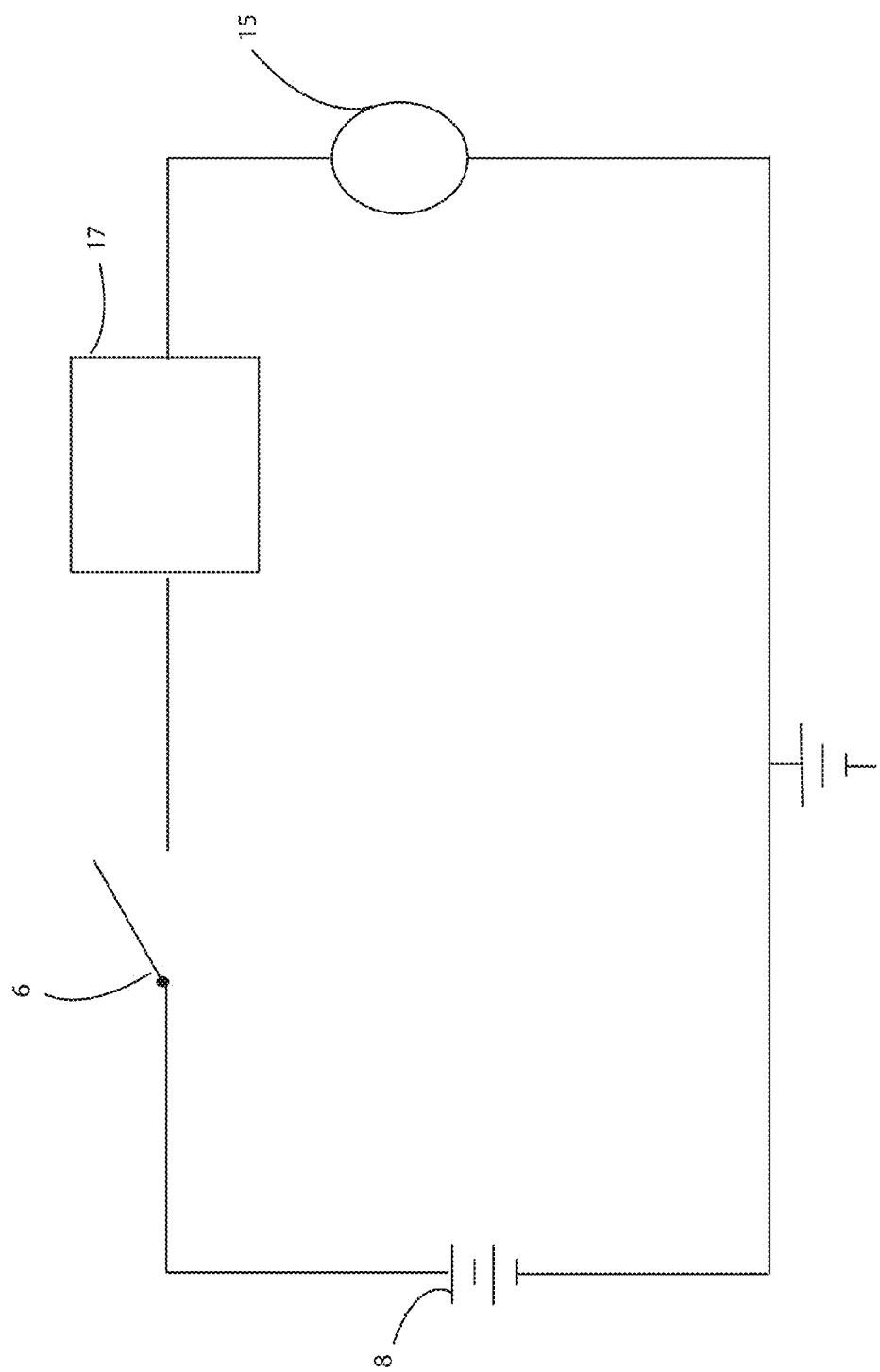
FIG. 3 is a functional schematic view of a circuit of the component shown in FIG. 2.

Referring to FIG. 3 there is shown a circuit having the battery 8 in series with a switch 6 which is actuated by a momentary pressing of pushbutton 7. Connected in series between the switch 6 and blower 15 is the timer circuit 17.

When the switch 6 is closed by pressing pushbutton 7, a circuit is completed between the nine volt battery 8, timer circuit 17, and fan 15. The application of voltage to the timer circuit allows current to be conducted from the battery through the timer circuit to the fan for turning the fan on.

The squirrel cage fan 15 is a low inertia high speed fan which is capable of reaching its full speed of 20,000 RPM within 1.5 seconds after it is powered on. The "instant on" high speed propeller of fan 15 discharges a short duration burst of air. The ability of the fan 15 to quickly reach maximum rotational velocity can extend the life of battery 8 well beyond the typical shelf life of 4-6 weeks for a point of sale display unit so that the battery 8 does not require replacement.

The timer circuit automatically turns off within 5-6 seconds after actuation thereby opening the circuit between the battery 8 and fan 15 unless sooner actuated again. Once power to the fan is interrupted, the low inertia propeller of the blower fan 15 comes to quick stop. The timer circuit 17 then opens and remains open until the switch 6, after being opened in response to release of pushbutton 7 is momentarily closed by reactuating pushbutton 7. Analog timer devices suitable for service as timer 17 may be based on a monostable multivibrator or digital timers including oscillators and counters may be used as will be known to those skilled in the art.

The short duration burst of scented air exiting the port 9 in response to the on/off cycling of the fan 15 produces sufficient vapor to be sensed by a consumer standing near the point of purchase display 1, e.g. within 6 inches of the display. However, before the short burst of scented air can travel beyond that distance from the display, it is quickly dispersed and dissipated within the ambient atmosphere and becomes too diluted to be sensed by other customers and personnel within the store.

This localized emission of the fragrance scent makes sampling a personal experience without interfering with other products offered in the nearby in the same store or department. For example, if the point of purchase display 1 is used in a cosmetics store or in a cosmetics department of a department store there may be other perfume products for sampling nearby. The present invention enables each of the perfume products to be sampled in an open space without interfering with another.

Figure 4:
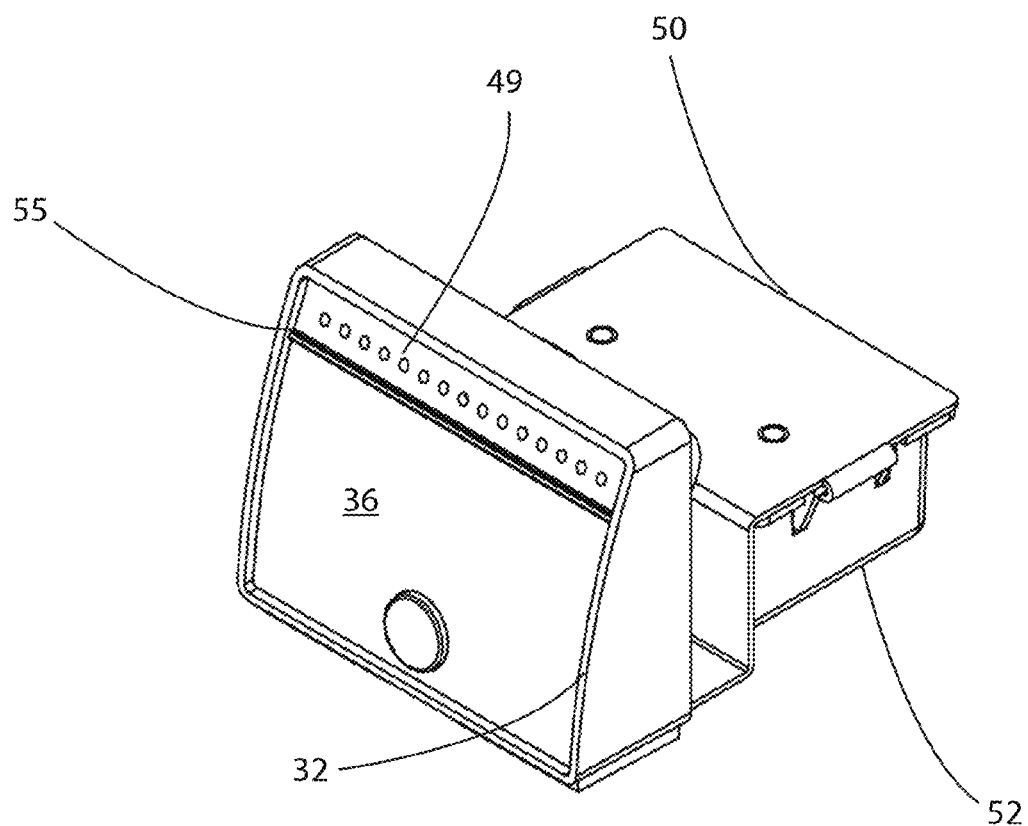
FIG. 4 is a perspective view of a second preferred embodiment of the invention.
Figure 5:
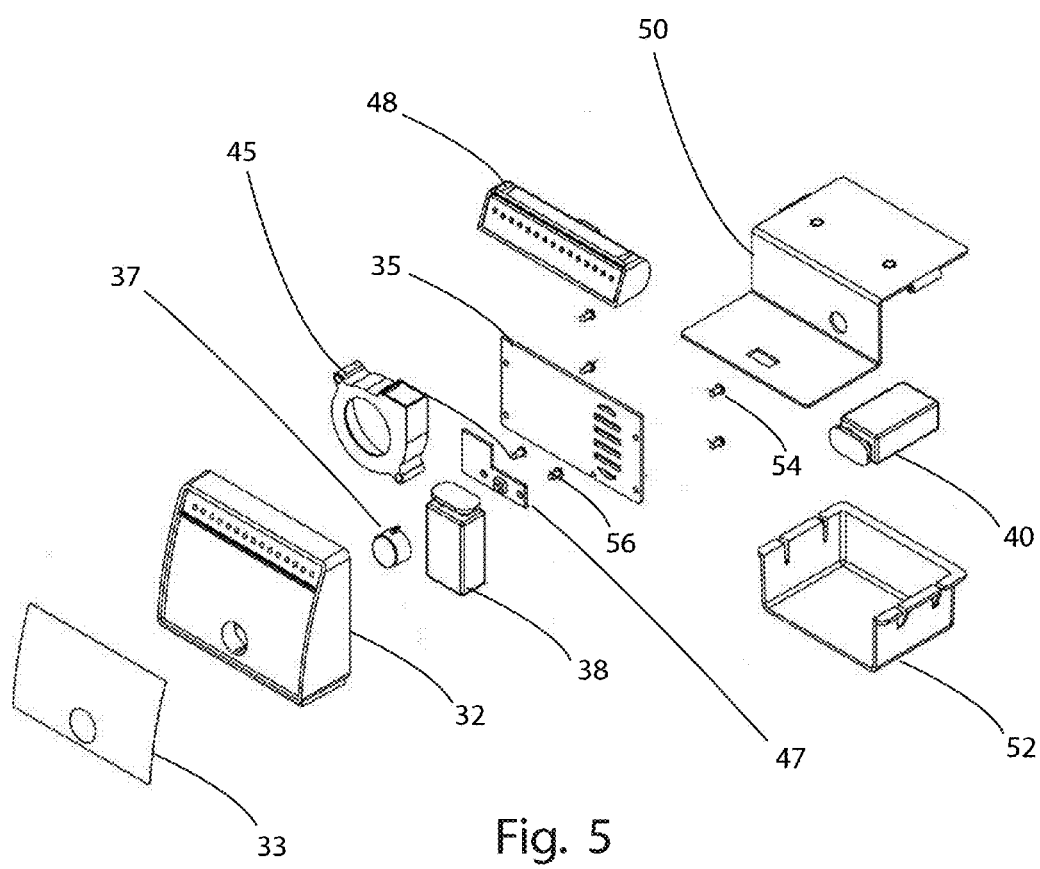
FIG. 5 is an exploded perspective view of the second preferred embodiment of the invention.
Figure 6A:
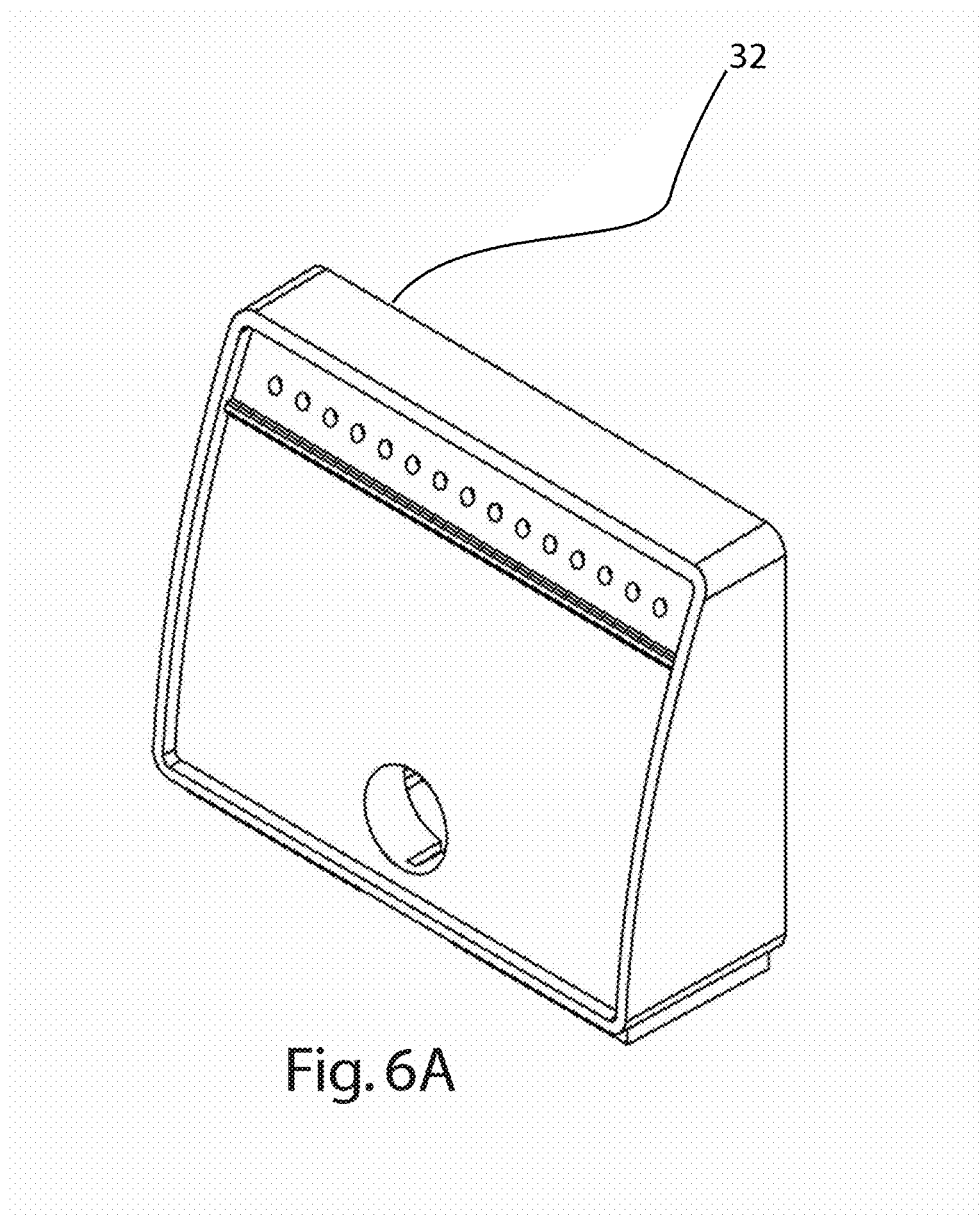
FIG. 6A is a perspective view of a component of the second preferred embodiment of the invention.
Figure 6B:
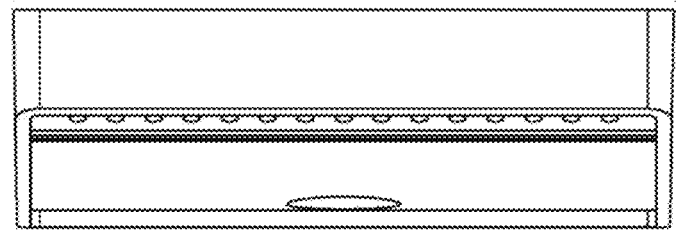
FIG. 6B is a top view of the component of the second preferred embodiment of the invention shown in FIG. 6A.
Figure 6C:
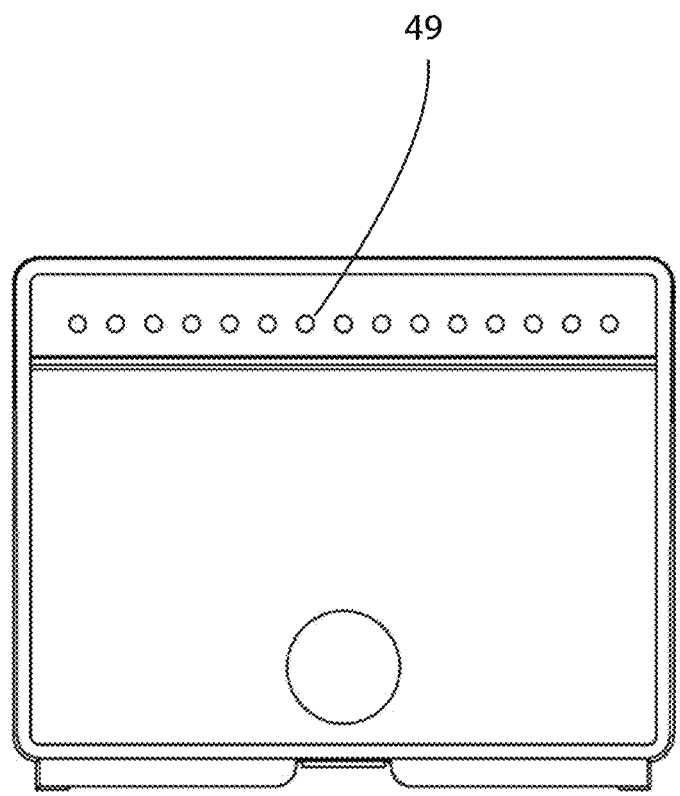
FIG. 6C is a front elevation view of the component of the second preferred embodiment of the invention shown in FIG. 6A.
Figure 6D:
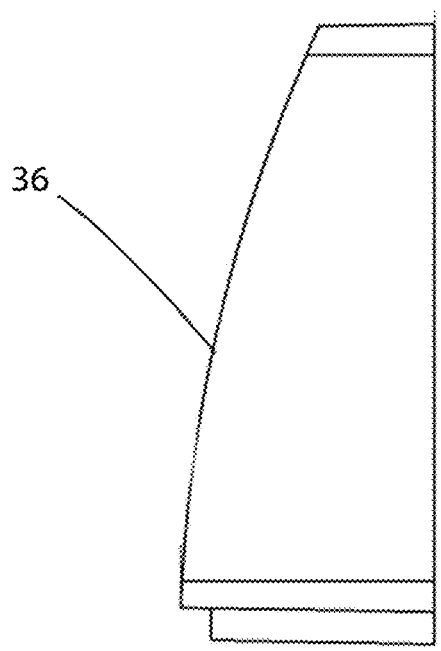
FIG. 6D is a side elevation view of the component of the second preferred embodiment of the invention shown in FIG. 6A.

Referring now to FIGS. 4 and 5 of the drawings there is shown a second preferred embodiment of the combination scent sampler and display unit 31 of the invention. The combination scent sampler and display unit 31 has a housing 32 with a substantially rectangular front facing, downward and outward sloping panel 36 to which an adhesive label 33 having an advertiser's graphics and/or text message can be affixed.

Referring additionally to FIGS. 6A-6D, the housing 32 is preferably injection molded in a polypropylene material. In addition to housing the scent pod 48, the front facing panel 36 also contains a blower fan, an electronic activation circuit, a pushbutton 37, and a battery 38 to power the fan of blower 45.

The front facing panel 36 of the combination scent sampler and display unit 31 performs the aesthetic function of providing the combination scent sampler and display unit 31 with a pleasing sculpture and the utilitarian function of providing support for a scent pod mounted atop the housing 32 of the combination scent sampler and display unit 31.

The housing 32 has a horizontal raised rib separating the front facing panel 36 into a lower portion on which the label 33 is mounted and an upper portion with a horizontal row of exhaust holes or ports 49.

Figure 7:
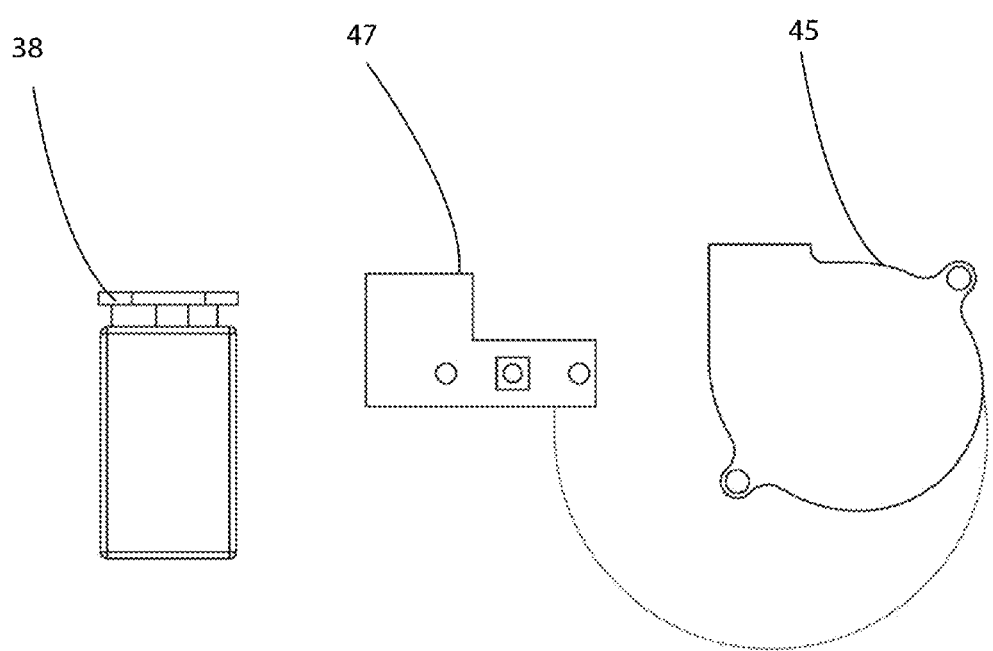
FIG. 7 is a schematic diagram showing the relationship among other components of the second preferred embodiment of the invention shown.

Referring to FIG. 7, disposed within a chamber in the housing 32 behind the front facing panel 36 is a blower 45 connected to an actuation circuit on a circuit board 47 which is affixed to the housing 32 by two screws 56. The blower 45 is powered by a conventional 9 volt battery 38 that is also within the chamber of housing 32. The circuit can electrically be the same as used in the first embodiment and illustrated in FIG. 3.

A spring biased switch in the activation circuit on the board 47 is aligned with a pushbutton 37 slidably mounted within an aperture centered in the front facing panel 36 beneath the label area. The chamber in the housing 32 is closed by attachment of a rectangular back cover 35 having four holes near its respective corners for receiving four screws 54 which are threaded into the rear of housing 32. &&&&

The scent pod 48 for containing a fragrance material is seated on a ledge in the chamber of the housing 32. The scent pod 48 is preferably injection molded in a polypropylene material. The primary use of the scent pod 48 is to contain scented beads or pellets in a manner such that when forced air is blown through an inlet opening, the air forces scent molecules that are emitted from the scent beads through a series of narrow openings in the front of the scent pod 48. The scent pod 48 is molded in a conventional manner but has a folding door 51 with a living hinge that allows the scent pod 48 to be molded in one piece rather than having a separate pod and door 51.

The combination scent sampler and display unit 31 is mounted on a bracket 50 which can be attached to a shelf in a retail store where the combination scent sampler and display unit 31 is to be installed.

A tray 52 is provided for storing a spare battery 40. The tray 32 may be attached to the bracket 50.

The content of the displayed graphics and message on the label 33 may be composed to promote the scented products being offered for sale at a point of purchase in a drug store, supermarket, cosmetics store or cosmetics department of a department store, whereat the combination scent sampler and display unit 31 is situated. In addition to cosmetics, the combination scent sampler and display unit 31 may also be used to sample personal hygiene products, home air-care products, and laundry products. The die-cut printed label 33 is applied to the outside face of the front facing panel 36 in a defined area below the horizontal rib 55 that is limited by raised ribs and a relief created by an aperture for receiving a pushbutton 37. The edges of the label 33 are inwardly spaced from, but close to, the edges of front facing panel 36 so that label 33 may be applied to and aligned with the front surface of the front facing panel 36.

A horizontal row of exhaust ports 49 in the form of round holes is formed proximate the top of the front facing panel 36 between the uppermost edge of the front facing panel 36 and horizontal rib 55 spaced below and running parallel to the front facing panel uppermost edge.

The pushbutton 37 is preferably injection molded in a polypropylene material. The primary use of the pushbutton 37 is to provide a plunger that activates a tactile switch on the circuit board 47 which, in turn, activates the fan of blower 45.

Figure 8A:
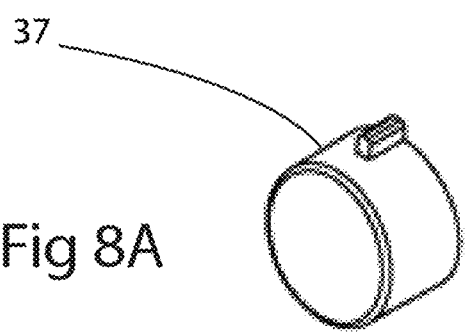
FIG. 8A is a perspective view of still another component of the second preferred embodiment of the invention.
Figure 8B:
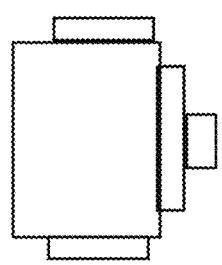
FIG. 8B is a side elevation view of the component of the second preferred embodiment of the invention shown in FIG. 8A.

Referring to FIGS. 8A and 8B, pushbutton 37 has two longitudinal guide fins that extend from the top and bottom 180 degrees apart and run axially substantially the entire length of pushbutton 37. The guide fins prevent rotation of the button about its axis when it is slidably mounted in the front panel aperture in the front facing panel 36. The cross section of the pushbutton 37 in a plane transverse to its axis is geometrically similar to the aperture in the front facing panel 36 and but slightly smaller in order to allow reciprocation of the pushbutton 37 within the aperture in the front facing panel 36 without binding, while preventing rotation of the pushbutton 7 about its axis.

The rear end of pushbutton 37 has a protrusion that aligns exactly with the actuator of a tactile switch on a circuit board 47 disposed behind the front facing panel 36 and within the housing 32 of the sampler/display unit 1 so that engagement of the pushbutton 37 by a shopper activates the tactile switch. The front-to-back dimension of the pushbutton 37 is such that when it is pushed by the shopper it activates the tactile switch and simultaneously comes to a positive stop rest on the circuit board 47.

The blower control circuit is mounted on PC board 47 which contains the electronics necessary to interface with the battery 38 and the blower 45. The physical aspects of the PC board 47 are such that the geometry describes an area where circuitry is permitted and an area where circuitry is prohibited. The PC board 47 also describes two through holes used to mount the PCB to the corresponding screw bosses inside the front facing panel.

The PC board 47 contains a programmable controller that directs the on time of the fan of blower when powered. The chip may be programmed to allow a specific current draw from the battery 38, a function of time, that is appropriate for the scent application required.

The area of the PC board 47 where circuitry is prohibited allows for a limiting stop for the Pushbutton 37.

The PC board 47 is attached to front facing panel via two screws 56 that insert through the rear of the PC board 47 and into corresponding screw bosses that are molded features contained on the inside surface of the front facing panel. The height of the screw bosses is of a height determined by the combined relationships of the tactile switch height relative to the front surface of the PC board 47, the height of the internal boss of the Pushbutton 37, and the amount of "throw" required to engage the electronics via the tactile switch.

The PC board 47 has a zone where components are prohibited from being mounted. This allows the back surface of the Pushbutton 37 to engage the limiting position of the PC board 47 at a precise moment. This moment allows for the engagement of the tactile switch but not past the point where it engages. The rigid nature of the PC board 47, 0.060" phenolic, when screwed to the positioning bosses inside The front facing panel, is of sufficient stiffness to stop the movement of the Pushbutton 37 in its activation direction.

Figure 9A:
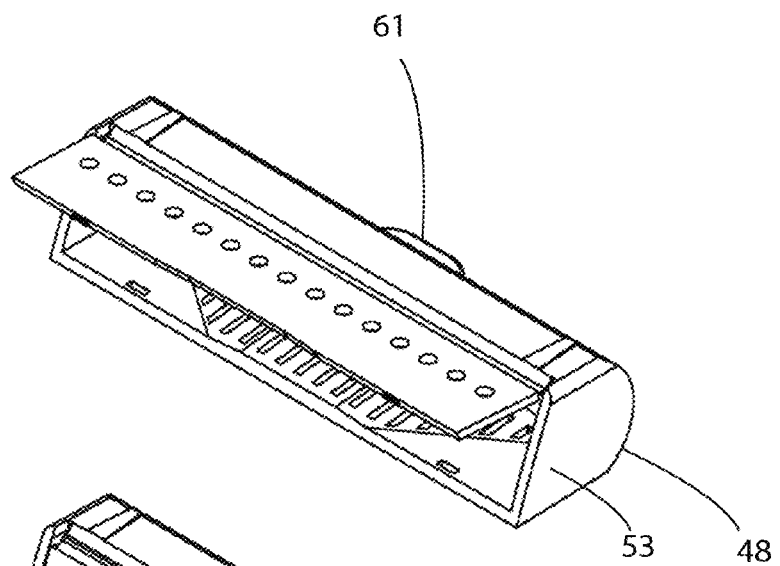
FIG. 9A is a perspective view of a further component of the second preferred embodiment of the invention in one disposition.
Figure 9B:
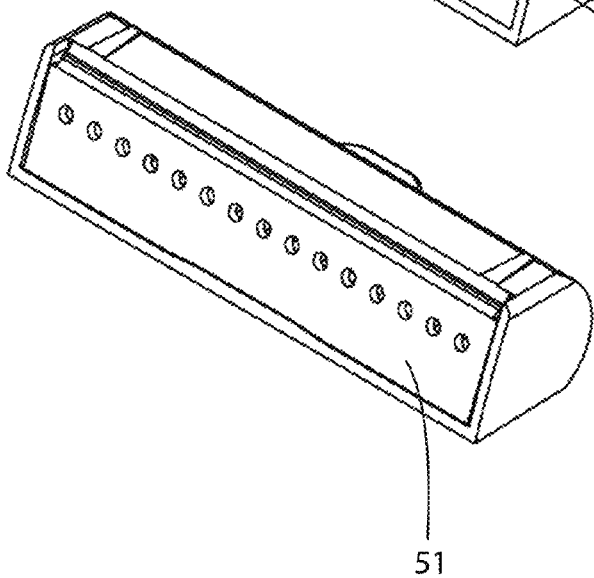
FIG. 9B is a perspective view of the further component of the second preferred embodiment of the invention shown in FIG. 9A in an alternate disposition.
Figure 9C:
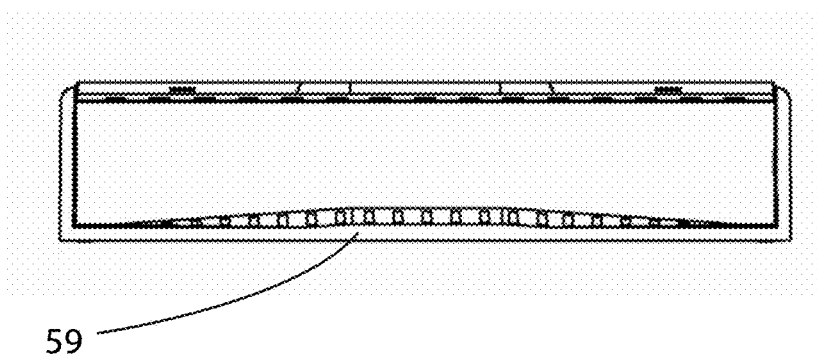
FIG. 9C is a front elevation view of the component of the second preferred embodiment of the invention in the deposition shown in FIG. 9B.

Referring now to FIG. 9A-9C, the scent pod has a front facing door 51 that is hinged along its upper edge to a housing 53 of the scent pod 48 which acts as a reservoir that can be filled with scented beads or pellets when the door 51 is open. The door 51 can be latched closed once scent beads or pellets have been added. The scent pod door 51 is suspended from a molded living hinge.

After the scent pod 48 has been filled with scented beads and the scent pod door 51 has been latched closed, the scent pod 48 is inserted into a rear opening in the combination scent sampler and display unit housing 32 behind the front facing panel of the combination scent sampler and display unit 31.

Referring to FIG. 9C, the scent pod 48 has a floor 59 with a series of slotted openings in its surface. The floor 59 has an arcuate cross section has is raised at its center for causing the forced air from the fan of blower 45 to spread out, permeate the scented beads within the scent pod 48, and exit through a series of horizontally aligned round holes that are molded into the door 51 of the scent pod. When the door 51 of the scent pod 48 is in a closed disposition, the round holes in the door 51 are in registration with the round hole exhaust ports 49 in the front facing panel. Thus, forced air originating with a momentary blast from the fan of blower 45 forces scent-laden air from the scent pod 48 through the registered openings in the door 51 of the scent pod 48 and the front facing panel.

The blower motor is a dc powered blower that is conventionally used to cool electronic circuit boards inside electronic products such as computers. This specific motor has ample capacity to produce the cubic feet per minute air flow needed to disperse the scent through the front of the finished assembly. The inflow of air to the fan of blower 45 is from the rear of the blower; the outflow of air from the blower is from the top of the blower. The blower housing is rectangular in shape. There are electrical leads from the motor that connect to the circuit board 47.

There is a mounting boss on the inside surface of the front facing panel that corresponds with a through hole in a portion of the RF-5015 blower fan. When the motor is placed on the mounting boss it is positioned such that it can be rotated but not moved laterally. The rectangular geometry of the outflow area of the motor is such that it engages a rectangular molded feature on a horizontally oriented rib inside front facing panel. The position of the motor is now restricted so that it is in a fixed position, that position being proper to force moving air through the scent pod 48. There are two raised rib bosses contained on the inside wall of the front facing panel that limit forward movement of the blower motor.

The housing of the combination scent sampler and display unit 31 has a rear opening through which the scent pod 48 may be inserted and moved forwardly into engagement with a rear face of the front facing panel 36. The height of a floor of the rear opening on which the scent pod 48 is supported has an elevation at which the holes in the door 51 of the scent pod 48 are in registration with the exhaust ports 49 in the front facing panel 36.

One or more raised ribs may be provided on the floor, ceiling, or interior side wall surfaces of the rear opening, or on the outer surfaces of the scent pod 48 for frictional engagement between the scent pod 48 and housing rear opening to lightly secure the scent pod 48 in place but enable withdrawal of the scent pod 48 from the housing 32. For the latter purpose the scent pod 48 has projecting from its rear surface a tab 61 which can be grasped between two fingers for pulling the scent pod 48 rearwardly and out of the housing 32 to enable the scent pod 48 to be filled or refilled with scented beads of pellets. Thus, the outer profile of the scent pod 48 is substantially congruent to the upper chamber in the housing 32 behind the front facing panel thereby enabling the scent pod 48 to be inserted into the housing behind the front facing panel and securely held, but not locked into place.

The outer bottom surface of the front facing panel is shaped to conform to a sheet metal bracket 50 that allows the housing 32 to be mounted on a shelf in a retail store. The mounting bracket 50 is preferably laser-cut from 16 gauge sheet steel and formed with a generally Z-shaped profile.

The principal purpose of the mounting bracket 50 is to provide a very strong frame on which the molded components can be attached. Additionally, it provides for attachment of the combination scent sampler and display unit 31 to a retail in a very rigid manner, e.g., through the use of bolts. While the dimensions of the horizontal sections and the vertical section can be altered to accommodate specific shelf geometries, the basic shape of the bracket 50 preferably remains the same. The height of the vertical section, for example, would, if increased, lower the combination scent sampler and display unit 31 relative to the shelf on which it is mounted. This may be a desirable feature where a product marketer wants a specific visual clearance for viewing the products directly behind the combination scent sampler and display unit 31.

Figure 10A:
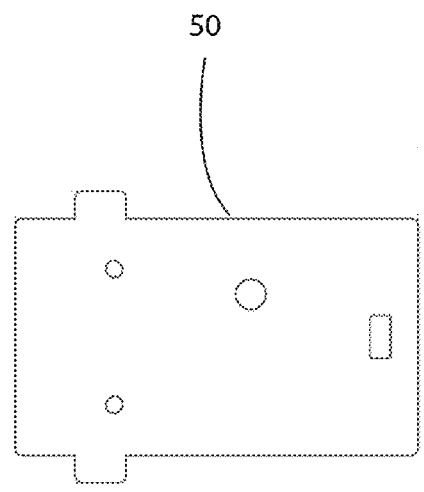
FIG. 10A is a top plan view of still a further component of the apparatus of the second preferred embodiment of the invention in one disposition.
Figure 10B:
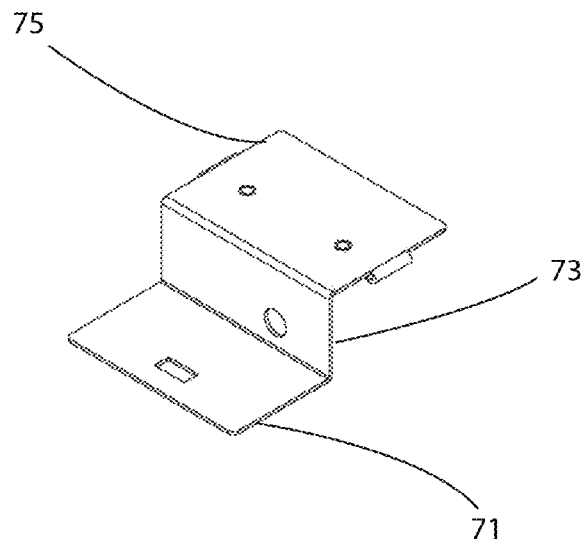
FIG. 10B is a perspective view of the component of the second preferred embodiment of the invention shown in FIG. 10A in an alternate disposition.

Referring to FIGS. 10A and 10B, when viewed from the right side, three planar sections of the Z-shaped bracket are as follows. A lower horizontal section 71 of the bracket 50 is designed to fit into a corresponding slot in the rear of the base of the housing 32. This section of the bracket 50 also contains a rectangular hole. The hole is designed to ride over and then catch a wedge-shaped protrusion on the lower surface of the housing 32.

When combination scent sampler and display unit 31 is attached to the mounting bracket 50 the side edges of the mounting bracket 50 are guided by the side walls and the flanged surfaces of the base of combination scent sampler and display unit 31. This prevents any movement, laterally or vertically, between the bracket 50 and housing 32. As the leading edge of the mounting bracket is further advanced into the base of the combination scent sampler and display unit 31 of front facing panel it rides over a wedge-shaped projection where the tangent edge of the wedge is encountered first. As the mounting bracket 50 is further pushed into the base of the combination scent sampler and display unit 31 it reaches a point where the rear edge of the wedge is allowed to flex into position within the rectangular hole in the mounting bracket 50 where is it captured. When the wedge on the base of the combination scent sampler and display unit 31 is fully contained within the perimeter of the rectangular hole of the mounting bracket 50, the combination scent sampler and display unit 31 is positioned as intended.

The height of the wedge on the base of the combination scent sampler and display unit 31 can be increased to provide a more secure retention in the bracket or decreased to facilitate removal of the combination scent sampler and display unit 31 from the mounting bracket 50 if required. There is a theoretical limit to the height of the wedge shape in that it could surpass the elasticity inherent in the plastic to allow for a positive engagement. Conversely, there is a minimum height relationship in the height of the wedge that could render the engagement to be insufficient to secure the front facing panel to the mounting bracket 50.

A vertical planar section 73 of the bracket has a height that determines the elevation of the combination scent sampler and display unit 31 relative to the shelf on which it is mounted. As the height of the vertical bracket section is increased, the position of the combination scent sampler and display unit 31 relative to the shelf on which it is mounted is lowered. The vertical section of the bracket 50 is provided with a through hole that allows for the passage of a power cord to a battery pack.

An upper horizontal section 75 of the bracket 50 has two through-holes located for registration with two corresponding holes or fasteners in or on a retail shelf. The diameters of the holes are sufficient to allow for the insertion of threaded inserts which allow for the attachment of the bracket 50 to the retail shelf. There are also two tabs extending from opposite sides of the upper section that, when bent inwardly, allow for mutual engagement between the bracket 50 and a spare battery tray 52.

A tray 52 for a spare battery 40 may optionally be provided for storing one or more batteries which may conveniently be accessed for replacing a spent battery 38. Alternatively, the batteries in the spare battery tray 52 may be wired in circuit with the battery 38 to provide extra current capacity and for extending the time between required battery changes.

Figure 11:
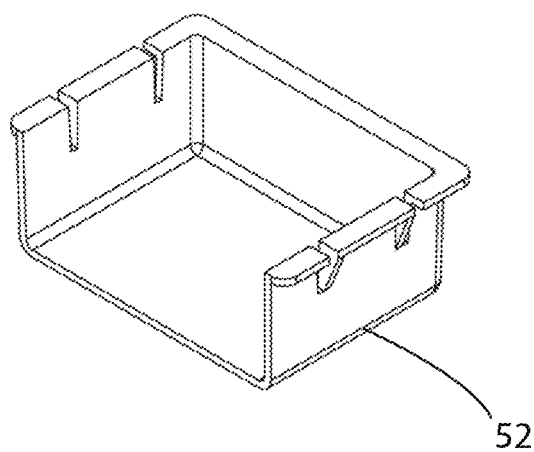
FIG. 11 is a perspective view of an additional component of the second preferred embodiment of the invention.

Referring to FIG. 11, the spare battery tray is preferably injection molded in a polypropylene. The physical shape of the spare battery tray 52 is a box-shape minus front and top walls. Running along the top wall sections is a flanged rib. The flanged rib is interrupted in symmetrically opposed areas to produce a spring, or snap-action that allows for the spare battery tray 52 to be contained within the corresponding tabs of mounting bracket 50. The height of the spare battery tray 52 is such that it does not protrude beneath the finished assembly but has a height tall enough to hold additional batteries.

The spare battery tray 52 has two tabs that can be inwardly squeezed far enough together to pass inside of the space between the corresponding tabs on mounting bracket 50. Additionally, there are two gusseted ribs on the edges of the tabs of the spare battery tray 52 which prevent front to back motion of the spare battery tray 52 once it has been engaged on the mounting bracket 50.

A rectangular back cover 35 for the combination scent sampler and display unit housing 32 is preferably injection molded in a polypropylene material. Back cover 35 is mounted over the opening in the housing 32 which leads to the lower chamber that contains the fan of blower 45 and electronics behind the front facing panel of the combination scent sampler and display unit 31.

An RF-5015 motor is mounted in the housing chamber and sized so that it is confined by the walls of the chamber and the back cover 35. The inner surface of back cover 35 and the RF-5015 motor are in close engagement when the back cover 35 is attached to combination scent sampler and display unit 31 with four screws 54.

Figure 12:
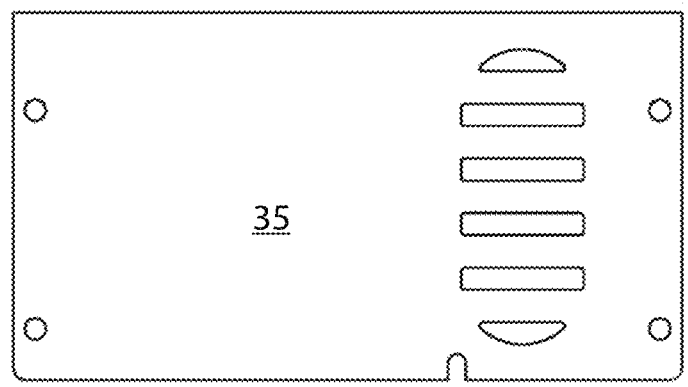
FIG. 12 is a front elevation view of a further additional component of the second preferred embodiment of the invention.

Referring to FIG. 12, the back cover 35 is rectangular and flat. It has four through holes for attachment with screws 54 to the combination scent sampler and display unit 31. The back cover 35 has a small "mouse-hole" opening extending from the front to rear face through which wires can pass. The back cover 35 is also vented to allow for movement or air from the ambient environment to the RF-5015 Motor.

Figure 13:
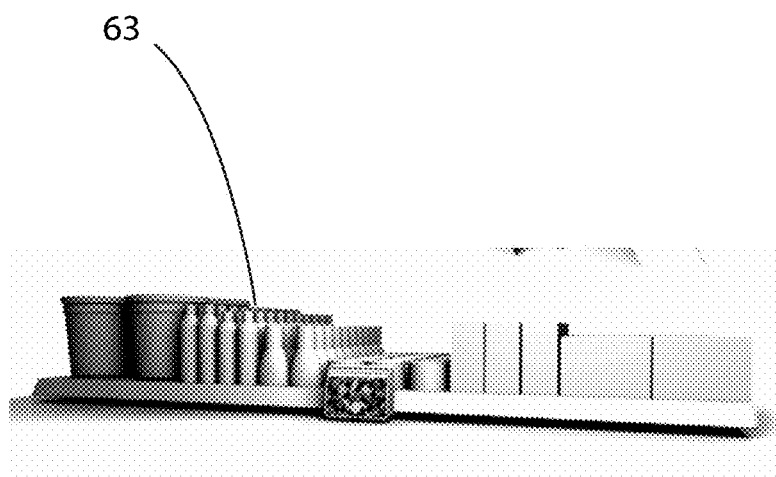
FIG. 13 is a perspective view of the second preferred embodiment of the invention shown in its intended environment.

Referring to FIG. 13, atop the shelf on which the combination scent sampler and display unit 31 is to be mounted are perfume bottles 63, or replicas thereof which simulate the appearance of actual containers of perfume, cologne, toilet water or other scented products. Normally the bottles 63 will not be functional but only illustrative of the actual scented product. That is, they will not be functional to spray a sample of the scented product contained in bottles. The perfume bottles or containers 63 may be affixed to the shelf to prevent easy removal in order to avoid pilferage.

It is to be appreciated that the foregoing is a description of a preferred embodiment of the invention to which variations and modifications may be made without departing from the spirit and scope of the invention.

What is claimed is:

1. A combination scent sampler and display unit comprising,
   a scent reservoir for housing scent material from which a fragrance can evaporate into the air therein, said air in said scent reservoir being scented air, said scent reservoir having at least one exhaust port,
   a blower including a motor and a fan mounted proximate said reservoir for blowing ambient air through said scent reservoir and scented air out of said exhaust port,
   a voltage source,
   an actuator connected in circuit between said motor and said voltage source and operable for turning on said blower,
   a timing circuit for turning off said blower a fixed time after said blower is turned on, whereby scented air is blown through said exhaust port for sampling said fragrance for a limited time following the turning on of said blower, and
   a scent pod mounted on said housing and containing said reservoir, said scent pod having an inlet opening in communication with said fan and a plurality of exhaust ports for dispersing scented air into the ambient environment.

2. A combination scent sampler and display unit according to claim 1 wherein said scent pod has an interior nonplanar surface for dispersing the air blown thereinto.

3. A combination scent sampler and display unit according to claim 2 wherein said scent pod has an interior convex floor for dispersing the air blown thereinto.

4. A combination scent sampler and display unit according to claim 1 wherein said housing has an interior supporting surface for receiving said scent pod therein with the exhaust ports in said scent pod in registration with the exhaust ports in said front facing panel.

5. A combination scent sampler and display unit according to claim 4 wherein said scent pod has a door which can be opened for filling said scent pod with scented material and closed for fitting said scent pod into said housing, said exhaust ports in said scent pod being in said door, said housing preventing said door from opening when said scent pod is mounted therein.

6. A combination scent sampler and display unit according to claim 1 wherein said timing circuit comprises an RC circuit.

7. A combination scent sampler and display unit according to claim 1 wherein said timing circuit comprises a monostable multivibrator.

8. A combination scent sampler and display unit according to claim 1 wherein said timing circuit comprises a digital timer.

9. A combination scent sampler and display unit comprising,
   a housing,
   a chamber in said housing for containing a fragrance material, said chamber having an exhaust opening to the ambient environment,
   a blower mounted in said housing for blowing air through said chamber,
   a voltage source disposed in said housing,
   a control circuit for operatively connecting said voltage source to and disconnecting said voltage source from said blower, said blower forcing scented air through said chamber to said exhaust opening,
   said control circuit comprising an actuator and a timing circuit, said timing circuit connecting said voltage source to said blower in response to operation of said actuator and said timing circuit disconnecting said voltage source from said blower a predetermined time after operation of said actuator, and
   a scent pod removably mountable in said chamber, said scent pod having an inlet port in communication with an outlet of said blower when mounted in said chamber, and an outlet port, said scent pod being fillable with said fragrance material for scenting the air in said scent pod, said blower, when connected to said voltage source, forcing air through said scent pod for enabling sampling of a scent of said fragrance material outside of said scent pod proximate said outlet port.

10. A combination scent sampler and display unit according to claim 9 wherein said scent pod has a perforated hinged door covering an opening into said chamber when closed, and said housing has a perforated wall proximate said door when said scent pod is mounted in said chamber, whereby said blower can force air through said scent pod, said door and said wall to the ambient environment for sampling said fragrance.

* * * * *